(12) United States Patent
Su et al.

(10) Patent No.: US 7,695,899 B2
(45) Date of Patent: Apr. 13, 2010

(54) METHODS OF IDENTIFYING AND USING CHEMOTHERAPEUTIC AGENTS

(75) Inventors: Tin Tin Su, Boulder, CO (US); Burnley R. Jaklevic, Longmont, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 249 days.

(21) Appl. No.: 10/978,206

(22) Filed: Oct. 29, 2004

(65) Prior Publication Data
US 2005/0123963 A1    Jun. 9, 2005

Related U.S. Application Data

(60) Provisional application No. 60/515,723, filed on Oct. 29, 2003.

(51) Int. Cl.
*C12Q 1/00* (2006.01)
(52) U.S. Cl. ......................................................... 435/4
(58) Field of Classification Search .................... 514/1; 435/4
See application file for complete search history.

(56) References Cited

U.S. PATENT DOCUMENTS

| | | | |
|---|---|---|---|
| 5,972,640 A | 10/1999 | Drubin et al. | |
| 6,489,127 B1 | 12/2002 | Duyk et al. | |
| 6,511,818 B2 | 1/2003 | Vogelstein et al. | |
| 6,723,498 B1 | 4/2004 | Shyjan et al. | |

OTHER PUBLICATIONS

Simon et al (Cancer Research, 2000, 60:328-333).*
Gura (Science, 1997, 278:1041-1042.).*
Powell et al (Cancer Research, Apr. 1995, 55: 1643-1648).*
Peters et al (PNAS, Aug. 2002, 99(17): 11305-11310).*
Jin et al (PNAS, Jun. 2000, 97(13):7301-7306).*
Geoerger et al (British Journal of Cancer, Aug. 2003, 89: 577-584).*
Vassal et al (Cancer Chemother Pharmacol, 2003, 51: 385-394).*
Asakawa et al (Anticancer Research, Jul.-Aug. 2002; 22(4): abstract).*
Takahashi et al (Int J Hyperthermia, Mar.-Apr. 2003, 19(2): abstract).*
Hasegawa et al (Radiat Med, May-Jun. 1997; 15(3): abstract).*
Chehab et al., (2000) Genes Dev. 14: 278-288.
Dasika et al., (1999) Oncogene. 18(55):7883-99.
Elledge, (Dec. 1996) Science 274: 1664-1672.
Hafen & Stocker, (2003) PloS Biology 1: 319-323.
Harper et al., (Apr. 1995) Mol. Biol. Cell 6: 387-400.
Hirao et al., (Mar. 2000) Science 287:1824-1827.
Jaklevic & Su, (Jan. 2004) Curr. Biol. 14: 23-32.
Johnston & Gallant, (2002) Bioessays 24: 54-64.
Lopez-Girona et al., (Jan. 2001) Curr. Biol. 11:50-54.
Motoyama & Naka, (2004) Curr. Op. Gen. Dev. 14: 11-16.
Oldham & Hafen, (Feb. 2003) Trends Cell Biol. 13(2):79-85.
Sancer et al., (2004) Ann. Rev. Biochem. 73: 39-85.
Shieh et al., (2000) Genes Dev. 14: 289-300.
Stocker & Hafen, (2000) Curr. Op. Gen. Dev. 10: 529-535.
Wassmann and Benezra R. (2001) Cuff Opin Genet Dev. 1l(1):83-90.
Zhou & Elledge, (Nov. 2000) Nature 408:433-439.
Nojima H. (Dec. 1997) Hum Cell 10(4):221-30.
McDonald and El-Deiry (2001) Ann Med. 33(2):113-122.
Brugarolas et al. (Oct. 1995) Nature 377:552-557.
Dotto & Silke (2004) Dev. Cell. 7:2-3.
Lopez-Girona et al. (Jan. 1999) Nature 397:172-175.

* cited by examiner

*Primary Examiner*—Sean E Aeder
(74) *Attorney, Agent, or Firm*—Townsend and Townsend and Crew LLP

(57) ABSTRACT

The disclosure includes methods for the identification of chemotherapeutic agents that selectively reduce the growth or the survival of genotoxically stressed DNA damage checkpoint deficient tissue, such as irradiated cancerous tissue. The methods involve the use of genotoxically-stressed tissue(s) that are deficient in one or more DNA damage checkpoints. The disclosure also provides kits for performing the disclosed methods. The disclosure also includes chemotherapeutic agents that selectively reduce the growth or the survival of genotoxically stressed DNA damage checkpoint deficient tissue, such as irradiated cancerous tissue. The disclosure also includes methods of treatment or management of cancer, tumor formation, other conditions involving abnormal proliferation, or cell-cycle diseases or disorders.

6 Claims, 1 Drawing Sheet

METHODS OF IDENTIFYING AND USING CHEMOTHERAPEUTIC AGENTS

RELATED APPLICATIONS

This application claims the benefit of U.S. Provisional Application Ser. No. 60/515,723, filed Oct. 29, 2003, incorporated herein by reference in its entirety.

This invention was made with Government support under Grant No. GM66441 awarded by the National Institutes of Health. The U.S. Government may have certain rights in this invention.

BACKGROUND OF THE INVENTION

Based on about three decades of research in yeast and vertebrate cells in culture, cell cycle regulation by checkpoints is believed to be of paramount importance in the survival of single cells challenged with genotoxins. The prior art, however, is less clear on whether cell cycle regulation by checkpoints is equally important for the survival of multicellular tissues, organs, and organisms that are similarly challenged.

In eukaryotes, DNA damage checkpoints monitor the state of genomic DNA and delay the progress through the cell division cycle (reviewed in Elledge, Science 274: 1664 (1996) and in Zhou & Elledge, Nature 408: 433 (2000). Components of the signal transduction pathway that constitute the DNA damage checkpoint are well-characterized and include, in mammals, two P13-like kinases, ATM and ATR, and two serine/threonine kinases, CHK1 and CHK2. Homologs of these kinases are found from yeast to worm to fly to human and assume similar roles where examined.

Much of current and recent work on DNA damage checkpoints has revealed in detail the molecular nature of their interface with the cell cycle machinery. For example, delay of G2/M transition in fission yeast is initiated when CHK1 phosphorylates CDC25, a phosphatase that activates cyclin dependent kinase 1 (CDK1). Phosphorylation of CDC25 by CHK1 allows the binding and inactivation of the former by a 14-3-3 protein, thereby keeping CDK1 in the phosphorylated and inactive form. This delays the entry into mitosis (Lopez-Girona et al., Nature 397: 172 (1999); Lopez-Girona et al., Curr. Biol. 11:50 (2001)). In another example, delay of S phase entry is elicited when Chk2 phosphorylates and stabilizes p53, which in turn promotes transcription of p21; p21 inhibits CDK2 to delay G1/S transition (Brugarolas et al., Nature 377: 552 (1995); Chehab et al., Genes Dev. 14: 278 (2000); Harper et al., Mol. Biol. Cell 6: 387 (1995); Hirao et al., Science 287:1824 (2000); Shieh et al., Genes Dev. 14: 289(2000)).

Mutational loss of DNA damage checkpoint function is associated with, and is a contributory factor in, many cancers. See for example, McDonald et al. ER 3rd, El-Deiry W S. Checkpoint genes in cancer. Ann Med. 2001 March; 33(2): 113-22; Wassmann K, Benezra R. Mitotic checkpoints: from yeast to cancer. Curr Opin Genet Dev. 2001 February; 11(1): 83-90; Molinari M. Cell cycle checkpoints and their inactivation in human cancer. Cell Prolif. 2000 October; 33(5):261-74; Dasika G K, Lin S C, Zhao S, Sung P, Tomkinson A, Lee E Y. DNA damage-induced cell cycle checkpoints and DNA strand break repair in development and tumorigenesis. Oncogene. 1999 Dec. 20; 18(55):7883-99; and Nojima H. Cell cycle checkpoints, chromosome stability and the progression of cancer. Hum Cell. 1997 December; 10(4):221-30, each of which is incorporated by reference. Agents that selectively kill or retard the growth of checkpoint-deficient tissues while sparing normal tissues are potential cancer therapeutic agents.

Screens for potential cancer therapeutic agents have typically been performed using single cells in culture. For example, U.S. Pat. No. 5,972,640 describes methods for contacting cultured cells that are deficient in a particular mitotic checkpoint with candidate agents in an attempt to identify agents that selectively arrest the growth of DNA damage checkpoint deficient cells. The behavior of such individual cultured cells, however, frequently differs dramatically from the behavior of tissues in response to the same agent. For example, it is possible that agents with the ability to arrest the growth of checkpoint deficient cells in tissues are not able to arrest the growth of those same checkpoint deficient cells when removed from the tissue context. Similarly, it is possible that agents with the ability to arrest the growth of checkpoint-deficient cells in culture are not able to arrest the growth of those same checkpoint-deficient cells in tissues. Thus, screens for agents that arrest the growth of checkpoint-deficient cells in culture can frequently misclassify therapeutic agents.

SUMMARY

The instant disclosure includes methods for identifying chemotherapeutic agents by genotoxically stressing a DNA damage checkpoint deficient tissue and genotoxically stressing a DNA damage checkpoint proficient tissue. The genotoxically-stressed tissues are contacted with a candidate agent (s). Candidate agents that reduce the survival or growth of at least part of the genotoxically-stressed checkpoint deficient tissue relative to the genotoxically-stressed checkpoint proficient tissue are identified as chemotherapeutic agents.

In one specific embodiment, the methods involve genotoxically stressing grp mutant larvae of *Drosophila melanogaster* and genotoxically stressing grp wild-type larvae of *Drosophila melanogaster*. The genotoxically-stressed larvae are contacted with a candidate agent(s). Candidate agents that reduce the survival or growth of genotoxically-stressed grp mutant larvae relative to genotoxically-stressed grp wild-type larvae are identified as chemotherapeutic agents.

Also included in the instant disclosure are chemotherapeutic agents that selectively reduce the growth or survival of genotoxically stressed DNA damage checkpoint deficient tissue, including, but not limited to, chemotherapeutic agents identified by the disclosed methods for identifying chemotherapeutic agents.

The disclosure also includes pharmaceutical compositions comprising a pharmaceutically-effective amount of a chemotherapeutic agent that selectively reduces the growth or survival of genotoxically stressed DNA damage checkpoint deficient tissue (including, but not limited to, chemotherapeutic agents identified by the disclosed methods for identifying chemotherapeutic agents) and further comprising one or more pharmaceutically acceptable carriers.

Also included in the disclosure are methods of treating diseases using chemotherapeutic agents that selectively reduce the growth or survival of genotoxically stressed DNA damage checkpoint deficient tissue (including, but not limited to, chemotherapeutic agents identified by the disclosed methods for identifying chemotherapeutic agents). For example, the disclosure includes a method of treatment which involves genotoxically stressing DNA damage checkpoint deficient tissue, such as cancerous tissue, and treating the DNA damage checkpoint deficient tissue with a chemotherapeutic agent. The chemotherapeutic agent reduces the survival or growth of at least part of the genotoxically-stressed DNA damage checkpoint deficient tissue relative to genotoxically stressed DNA damage checkpoint proficient tissue. The disclosure also includes a method of cancer treatment which involves genotoxically stressing cancerous tissue and treating said cancerous tissue with a chemotherapeutic agent identified by the disclosed methods for identifying chemotherapeutic agents.

Also included in the disclosure are kits comprising a DNA damage checkpoint deficient tissue, a DNA damage checkpoint proficient tissue, and instructions for at least one of: genotoxically stressing the DNA damage checkpoint deficient tissue, genotoxically stressing the DNA damage checkpoint proficient tissue, contacting the genotoxically-stressed tissues with a candidate agent; and determining whether the candidate agent reduces the survival or growth of at least part of the genotoxically-stressed checkpoint deficient tissue relative to the genotoxically-stressed checkpoint proficient tissue.

DETAILED DESCRIPTION OF THE PREFERRED EMBODIMENTS

Figure 1:
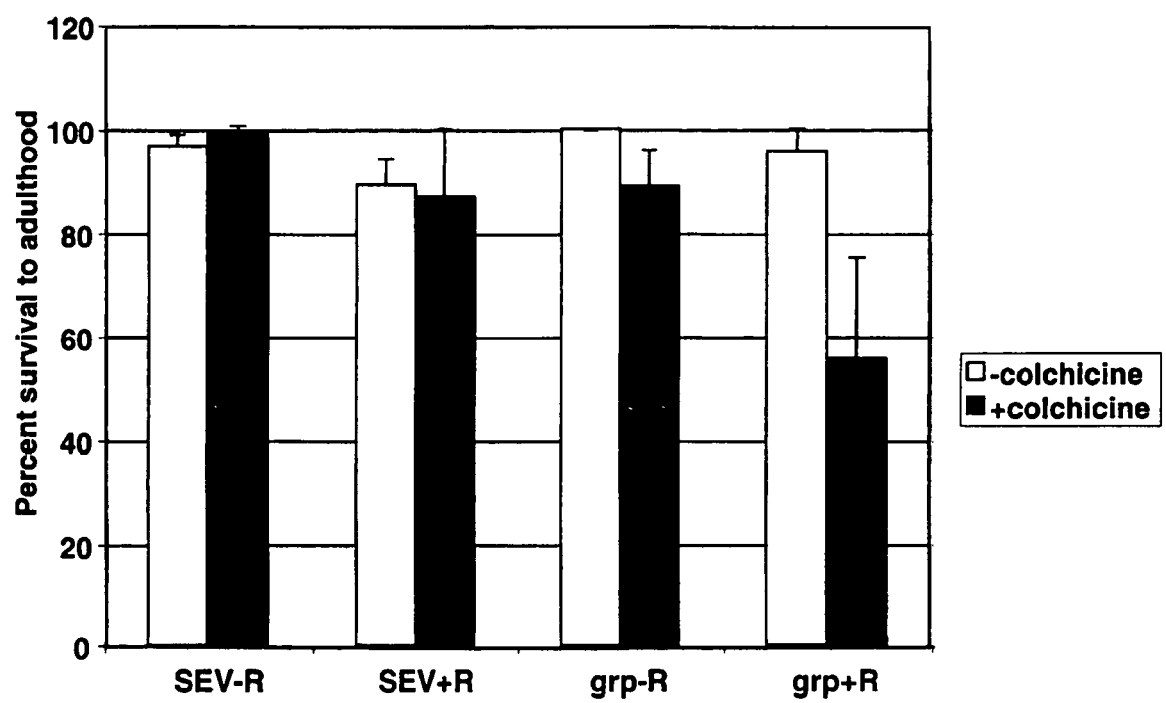
FIG. 1 illustrates that colchicine selectively reduces the survival of *Drosophila melanogaster* irradiated grp mutant larvae (grp+R) relative to non-irradiated grp mutant larvae (grp−R), wild-type irradiated larvae (SEV+R) and wild-type non-irradiated larvae (SEV−R).

All publications mentioned in this specification are hereby incorporated by reference to the same extent as if each independent publication or patent application was specifically and individually indicated to be incorporated by reference.

Throughout this application, unless otherwise indicated, wild-type gene names are written in lower case italics and capitalized nonitalics refer to proteins encoded by the wild-type gene.

As used herein, "checkpoint" is intended to mean a time-point in the cell cycle of a eukaryotic cell at which progression to a later stage in the cell cycle can be arrested or delayed in response to a stimulus or insult.

"DNA damage checkpoints" are checkpoints that are activated in response to DNA damage. Examples of such DNA damage checkpoints are the G1/S phase checkpoint, the intra-S phase checkpoint, the G2/M phase checkpoint, and the S/M checkpoint. The G1/S checkpoint prevents cells with DNA damage from initiating DNA replication. The intra-S phase checkpoint prevents cells in S phase with DNA damage from completing DNA replication. The G2/M checkpoint prevents cells with DNA damage from undergoing mitosis. The S/M checkpoint prevents cells that are blocked in S phase or are replicating DNA from undergoing mitosis.

"Checkpoint gene" is intended to mean a gene whose product (i.e., RNA or protein) is involved in regulating the progression through checkpoints in a eukaryotic cell.

"DNA damage checkpoint genes" are those genes whose products (i.e. RNA or protein) are involved in regulating progression through DNA damage checkpoints in response to DNA damage. Exemplary DNA damage checkpoint proteins include, but are not limited to, the following:

RFC-like proteins (including RAD 17 in mammals, RAD 17 in *Schizosaccharomyces pombe*, and RAD24 in *Saccharomyces cerevisiae*);
PCNA-like proteins (including RAD9, RAD1, AND HUS1 in mammals; RAD1, RAD9, and HUS1 in *Schizosaccharomyces pombe*; DDC1, RAD17, and MEC 3 *Saccharomyces cerevisiae*);
PI3-Kinases (including ATM and ATR in mammals; TEL1 and RAD3 in *Schizosaccharomyces pombe*; TEL 1, MEC 1 in *Saccharomyces cerevisiae*; and MEI41 in *Drosophila melanogaster*);
PI3-Kinase binding partners (including ATRIP in mammals, RAD26 in *Schizosaccharomyces pombe*, and DDC2/LCD1/PIE1 in *Saccharomyces cerevisiae*);
MDC1, 53BP1, TOPBP1, CLASPIN, and BRCA1 in mammals;
CUT5, MRC1, CRB2/RPH9 in *Schizosaccharomyces pombe;*
DPB11, MRC 1, and RAD9 in *Saccharomyces cerevisiae;*
CHK1, CH2 in mammals;
CHK1, CDS 1 in *Schizosaccharomyces pombe;*
CHK1, RAD53 in *Saccharomyces cerevisiae;* and
GRAPES in *Drosophila melanogaster*

"DNA damage" includes backbone breaks on one strand of DNA (also referred to as "nicks"), double-stranded backbone breaks, single-strand gaps, and abasic sites. DNA damage also includes stalled replication forks, base pair mismatches, and bubbles and loops formed by extensive base pair mismatches. DNA damage also includes DNA base damage, including, but not limited to, $O^6$-methyldeoxyguanosine, thymine glycols, reduced bases, oxidized bases, fragmented bases, cyclobutane pyrimidine dimers, and cisplatin G-G interstrand cross-links.

Illustrative methods by which DNA strand breaks can be introduced into chromosomal DNA include DNA ligase mutations, topoisomerase mutations, ionizing radiation (including X-radiation and gamma-radiation), and treatment with drugs (e.g., hydroxyurea), or treatment with chemotherapeutic agents, e.g., 5-fluorouracil, ectopside, and the like.

A "tissue" is an aggregate of cells, usually of a particular kind, that function together as a unit. Major tissue types include, but are not limited to, epithelial, connective, skeletal, muscular, glandular, and nervous tissue. Examples of tissues which fall within this definition include, but are not limited to, organs, skin, muscles, bone marrow, tumors, lymph nodes, arteries, etc. The term "tissue" refers to intact structures in an organism, as well as structures, or portions thereof, that have been removed from an organism, or have been transplanted from one organism to another organism of the same or different species, or transplanted from one site on an organism to a different site on the same organism.

The present disclosure includes methods for identifying chemotherapeutic agents, and also discloses methods of treating cancer, tumors, neoplasms and other proliferative disorders using those chemotherapeutic agents. The chemotherapeutic agents identified by the disclosed methods can be used, for example, to reduce the growth of cancerous tissues or tumors in an organism, completely arrest the growth of cancerous tissue or tumors in an organism, or kill cancerous tissue or tumors in an organism. The term "growth" means an increase in cell number, an increase in cell mass, or an increase in both cell number and cell mass. Preferably, the chemotherapeutic agents of the disclosure do not have an effect on normal tissue or cells to any detrimental extent when administered in therapeutically effective amounts.

In one aspect, the disclosure discloses a method for identifying chemotherapeutic agents by genotoxically stressing at least one first tissue. At least some of the cells of this tissue lack at least one DNA damage checkpoint function. Such tissue is hereinafter referred to as "DNA damage checkpoint deficient tissue." The genotoxically-stressed DNA damage checkpoint deficient tissue(s) is treated with one or more candidate agents, before and/or during and/or after the genotoxic stress. At least one second tissue is also genotoxically-stressed and treated with the same candidate agent(s). The cells of this latter genotoxically-stressed tissue(s) possess the DNA damage checkpoint function that is missing in the DNA damage checkpoint deficient tissue, and is hereinafter referred to as "DNA damage checkpoint proficient tissue." The tissues are examined to identify candidate agents that have a differential effect at one or more concentrations on the survival or growth of at least part of the genotoxically-stressed DNA damage checkpoint deficient tissue(s) relative to the genotoxically-stressed DNA damage checkpoint proficient tissue(s) are identified as chemotherapeutic agents. A differential survival or growth effect can be determined by detecting reduced growth of at least part of the genotoxically-stressed DNA damage checkpoint deficient tissue(s) relative to the genotoxically-stressed DNA damage DNA damage checkpoint proficient tissue(s), slowed growth of at least part of the genotoxically-stressed DNA damage checkpoint deficient tissue(s) relative to the genotoxically-stressed DNA damage checkpoint proficient tissue(s), cessation of growth of at least part of the genotoxically-stressed DNA damage checkpoint deficient tissue, or death of at least part of the genotoxically-stressed DNA damage checkpoint deficient tissue.

The methods disclosed herein may be performed using a candidate agent at a plurality of different concentrations. Similarly, a candidate agent that is identified as a chemotherapeutic agent at a first concentration can be rescreened at a plurality of different concentrations to determine the concentration dependence of its activity and/or of the concentration dependence of its selectivity for genotoxically-stressed DNA damage checkpoint deficient tissue.

DNA damage checkpoint deficient tissue lacks at least one DNA damage checkpoint function in at least some of the cells that comprise the tissue. Such cells comprise at least one modification of one or more DNA damage checkpoint gene (s). The modification can be any type of mutation or alteration that hinders or destroys the ability of the gene product (i.e. RNA or protein) to halt or delay progression of the cell cycle in response to DNA damage relative to the wild-type gene product. The mutation can be in a coding sequence, or it can be in a non-coding sequence including an intron, an upstream promoter sequence, a downstream sequence, or a transcription activation site. The mutation can be, without limitation, a point mutation, a deletion or one or more base pairs, a translocation, an inversion, an insertion or one or more base pairs, or a duplication. The mutation can act genetically as, for example, a null, a hypomorph, or a gain of function mutation. The mutation can be maintained in homozygous form (the same mutation on each chromosome) or in heterozygous form (either a different mutation on each chromosome, or a mutation on one chromosome and a functionally wild-type gene on the other chromosome). The mutation can be a conditional mutation, such as a temperature sensitive mutation. The mutation can be carried by the endogenous copy of the DNA damage checkpoint gene in the organism comprising the tissue, or it can be carried by an additional copy of the gene which has been inserted elsewhere in the genome, or it can be carried by an additional copy of the gene which lies on an artificial vector, such as a plasmid, a cosmid, or an artificial chromosome.

The mutation can be induced by any method known in the art, including mutagen treatment of an organism comprising the wild-type gene, or through the manipulation of a functionally wild-type version of the gene (i.e. a version of the gene that produces a functionally wild-type product) using recombinant DNA techniques well known in the art. The mutation can occur spontaneously. In the case where the tissue is from a fruit fly, such as *Drosophila melanogaster*, the mutation can be caused by the insertion and/or imprecise excision of a transposon, such as a P-element transposon.

DNA damage checkpoint deficient tissue can also result from exogenous sequences that interfere with the function of the products (RNA or protein) of at least one DNA damage checkpoint gene. Such exogenous sequences include, but are not limited to, antisense sequences, small interfering RNA (siRNA) sequences that mediate RNA interference (RNAi) of the DNA damage checkpoint gene, or micro RNA (mRNA) sequences that mediate translational repression of the DNA damage checkpoint gene(s). The exogenous sequences can be maintained on and transcribed from an extrachromosomal element, such as a plasmid, artificial chromosome, or cosmid, or they can be maintained on and transcribed from a chromosome. The transcription of the exogenous sequences can be constitutive, or it can be inducible if an inducible promoter is used. Alternatively, the exogenous sequences may be directly delivered to the tissue. Methods for designing such exogenous sequences, for expressing those sequences in tissues, and for delivering those sequences to tissues are well known in the art.

Genotoxic stress can be exerted on DNA damage checkpoint deficient tissue and DNA damage checkpoint proficient tissue using any agent or treatment that damages DNA in such a way that a DNA damage checkpoint is triggered in DNA damage checkpoint proficient tissue. Suitable agents or treatments include ionizing radiation, such as X-rays, and chemical agents such as chemical mutagens. In preferred embodiments, genotoxic stress is exerted using an agent or treatment that causes single-strand or double-strand breaks in DNA. Single-strand or double-strand breaks can be induced conveniently using ionizing radiation such as X-rays. X-rays can be used, for example, at a dose of between about 1,000 Rads and about 10,000 Rads, more preferably between about 2,000 Rads and about 4,000 Rads. It is routine experimentation for one skilled in the art to select the appropriate sublethal dose of ionizing radiation required to induce activation of a DNA damage checkpoint.

The DNA damage checkpoint deficient tissue and the DNA damage checkpoint proficient tissue are comprised of tissue of a multicellular organism. The organism can be an invertebrate or a vertebrate. Suitable invertebrates include, but are not limited to, flies and nematodes. Suitable fly species include *Drosophila melanogaster*. Suitable nematode species include *Caenorhabditis elegans*. Suitable vertebrates include, but are not limited to, mice, hamsters, guinea pigs, rabbits, cats, dogs, cattle, sheep, pigs, horses, monkeys, chimpanzees, and humans.

In some embodiments all of the tissues of the multicellular organism are genotoxically stressed and/or treated with the candidate agent. In other embodiments, less than all of the tissues of the multicellular organism are genotoxically stressed and/or treated with the candidate agent. For example, if genotoxic stress is exerted by a chemical mutagen, then feeding the mutagen to the multicellular organism leads to many, if not all, of the tissues (which may be DNA damage checkpoint proficient or DNA damage checkpoint deficient) of the organism becoming genotoxically stressed. Alternatively, if a chemical mutagen is applied locally (e.g. topically), then only tissues in the locality of the point of application are genotoxically stressed. Similarly, if ionizing radiation is used to exert genotoxic stress it can be exerted locally (for example by using a focused X-ray source or the like) or it can exerted widely (for example using total body irradiation). The candidate agent can be applied using any appropriate method, including, but not limited to, parenteral administration, topical administration, oral administration etc depending on the identity of the multicellular organism.

In some embodiments, DNA damage checkpoint deficient tissue and DNA damage checkpoint proficient tissue can be in the form of a cultured explant. In other embodiments, the tissue(s) can be transplanted from one multicellular organism to another multicellular organism prior to genotoxic stress and/or treatment with the candidate agent, or it can be transplanted from a first site on a multicellular organism to a second site on the same multicellular organism prior to genotoxic stress and/or treatment with the candidate agent. For example, human tissue can be transplanted to a nude mouse strain, and the human tissue transplant is then treated with the candidate agent(s).

A multicellular organism can be a mosaic of (1) DNA damage checkpoint deficient tissue; and (2) DNA damage checkpoint proficient tissue. Alternatively, all of the tissues of a multicellular organism can be DNA damage checkpoint deficient, or all of the tissues of a multicellular organism can be DNA damage checkpoint proficient. The use of intact organisms comprising DNA damage checkpoint deficient tissue, DNA damage checkpoint proficient tissue(s), or both DNA damage checkpoint deficient and proficient tissue in the disclosed methods is expressly contemplated.

In some embodiments, the DNA damage checkpoint function is chosen so that DNA damage checkpoint deficient tissue is able to repair DNA damage caused by genotoxic stress, particularly DNA damage caused by ionizing radiation, such as single-strand breaks and double-strand breaks. It has been discovered by the inventors that such DNA damage checkpoint deficient tissue is able to survive DNA damage, but may suffer more cell death than DNA damage checkpoint proficient tissue. See Jaklevic & Su, *Curr Biol.* 14(1):23-32 (2004), incorporated herein by reference in its entirety. Compensatory cell proliferation may replace the cells lost by apoptosis or other forms of cell death in such DNA damage checkpoint deficient tissue. Without being bound to a particular hypothesis, the inventors believe that such DNA damage checkpoint deficient tissue is susceptible to candidate agents that interfere with the compensatory proliferation of cells that occurs in response to genotoxic stress. Since compensatory proliferation requires, among other processes, increased nutritional uptake, the use of DNA damage checkpoint deficient tissue in accordance with the methods disclosed herein allows for the identification of chemotherapeutic agents that interfere with nutritional uptake by genotoxically-stressed checkpoint deficient tissue. Such agents can also interfere to some degree with nutritional uptake in checkpoint proficient tissues and cells, but genotoxically-stressed checkpoint proficient tissues and cells are more tolerant of interference than genotoxically-stressed checkpoint deficient tissues and cells (such as tumor cells and cancer cells) which have an increased requirement for nutritional uptake in response to genotoxic stress.

In some embodiments, the genotoxically-stressed DNA damage checkpoint deficient tissue and the genotoxically-stressed DNA damage checkpoint proficient tissue are caused to have reduced cellular growth before and/or during and/or after treatment with the candidate agent(s). Without being bound by a particular hypothesis, it is believed that compensatory cell proliferation is required to survive genotoxic stress in DNA damage checkpoint deficient tissue, and that causing DNA damage checkpoint deficient tissue to have reduced growth will therefore further sensitize the tissue to genotoxic stress by at least partially preventing such compensatory proliferation. Reduced cellular growth can be caused by environmental factors, for example by maintaining the tissue and/or multicellular organism under nutritional stress. For example, *Drosophila melanogaster* larvae can be nutritionally stressed by feeding them on a sugar water diet or on a cornmeal-agar diet. Reduced cellular growth can also be caused by mutations in genes involved in directing cellular growth, for example by mutations in the genes involved in the Insulin-Like Growth Factor pathway (such as chico in *Drosophila*), the Rb/cdk4/cyclin D pathway, or mutations in the genes encoding RAS, MYC, and TOR proteins. The genes encoding these proteins are conserved across species, including between flies and mammals.

Chemotherapeutic agents identified according to the methods disclosed herein cause reduced survival or growth of genotoxically-stressed DNA damage checkpoint deficient tissue(s) relative to genotoxically-stressed DNA damage checkpoint proficient tissue(s). Reduced survival or growth can be manifest by reduced growth of at least part of a genotoxically-stressed DNA damage checkpoint deficient tissue(s) relative to genotoxically-stressed DNA damage checkpoint proficient tissue(s), slowed growth of at least part of a genotoxically-stressed DNA damage checkpoint deficient tissue(s) relative to genotoxically-stressed DNA damage checkpoint proficient tissue(s), cessation of growth of at least part of a genotoxically-stressed DNA damage checkpoint deficient tissue(s), or death of at least part of a genotoxically-stressed DNA damage checkpoint deficient tissue(s). The effects on the DNA damage checkpoint deficient and DNA damage checkpoint proficient tissue can be monitored directly by, for example, looking at the gross features of the tissue, or by looking at cell proliferation and morphology using a microscope in either fixed or unfixed tissue. Vital stains can used to differentiate between dead and living cells.

In some embodiments, tissue morphology is monitored in order to detect reduced survival or growth of genotoxically-stressed DNA damage checkpoint deficient tissue. Aberrant tissue morphology can be indicative of reduced growth of at least a part of the DNA damage checkpoint deficient tissue(s) relative to the DNA damage checkpoint proficient tissue(s), slowed growth of at least a part of the DNA damage checkpoint deficient tissue(s) relative to the DNA damage checkpoint proficient tissue(s), cessation of growth of at least a part of the DNA damage checkpoint deficient tissue, or death of at least a part of the DNA damage checkpoint deficient tissue. If the DNA damage checkpoint proficient or deficient tissue is involved in the generation of distinct structure(s) or organs during development in a multicellular organism, then the absence of those structures or organs, morphological defects in those structures or organs, or at least partial loss of function of those structures or organs can be monitored in order to identify candidate agent(s).

In some embodiments, the death or reduced fitness of a multicellular organism that comprises the genotoxically-stressed DNA damage checkpoint deficient tissue(s) is used as an indicator of reduced survival or growth of the tissue.

In one embodiment, DNA damage checkpoint deficient and DNA damage checkpoint proficient tissues from *Drosophila melanogaster* are employed. DNA damage checkpoint deficient *Drosophila* tissue(s) that results from mutations in the grapes gene (abbreviated "grp") is especially useful. *Drosophila* tissues that harbor grp mutations, including the $grp^1$ allele, are DNA damage checkpoint deficient but are able to survive genotoxic stress, such as ionizing radiation. Genotoxically-stressed grp mutant tissues appear to undergo increased cell death and compensatory proliferation relative to tissues that have wild-type grp function. It is believed that grp mutant cells are able to repair DNA damage.

*Drosophila* larvae or pupae that are mutant for the grp gene can be genotoxically stressed using sublethal doses of X-rays, for example using about 2,000-6,000 Rads of X-rays, most preferably using about 4,000 Rads of X-rays. The larvae or pupae can be treated with the candidate agents before and/or during and/or after the genotoxic stress, and the survival or growth of the larvae or pupae can be compared with that of genotoxically-stressed grp wild-type larvae or pupae that are treated with the same candidate agent(s). Survival or growth can be monitored by determining the number of larvae that become pupae, and/or by determining the number of pupae that eclose into adults (for example, by measuring the number of empty pupae cases). Candidate agents that reduce the survival or growth of genotoxically-stressed grp mutant larvae or pupae relative to genotoxically stressed grp wild-type larvae or pupae are identified as chemotherapeutic agents.

Grp mutant larvae can be further sensitized to genotoxic stress in this embodiment by nutritionally stressing the larvae before, during, or after genotoxic stress. Without limitation, larvae can be nutritionally stressed by feeding them on a sugar water diet, a cornmeal agar diet, or any other reduced nutrient diet. As described above, nutritional stress conditions further sensitize DNA damage checkpoint deficient tissue to genotoxic stress. Example 1 includes an exemplary and non-limiting protocol for an embodiment of the disclosed methods employing grp mutant larvae.

In another embodiment, mouse models of human tumors, well known in the art, are used in the methods disclosed herein. Such mouse models can be produced, for example, by implanting human tumors (or cells from such tumors) into mice, preferably into nude (athymic) mice or mice that otherwise lack the ability to distinguish between mouse tissue and implanted tissue. The implanted human tumor tissue is DNA damage checkpoint deficient. Genotoxic stress is exerted on the implanted human tumor using, for example, ionizing radiation or a chemical mutagen. The genotoxically-stressed tissue is treated with one or more candidate agents, for example by applying the agent directly to the tissue, or by administering the candidate agents parenterally to the mouse. Survival or growth of the tumor tissue at different times after treatment with the candidate agent(s) is monitored by detecting changes in the size or appearance of the tissue. The results are compared with the results obtained from treating genotoxically-stressed DNA damage checkpoint proficient tissue (such as normal human tissue of the same general type as the tumor tissue) with the same candidate agent(s), thereby allowing the identification of candidate agents that cause reduced survival or growth of genotoxically-stressed DNA damage checkpoint deficient tissue(s) relative to genotoxically-stressed DNA damage checkpoint proficient tissue(s).

Chemotherapeutic agents identified according to the methods disclosed herein may be further screened, for example, to determine if their effect is specific for genotoxically-stressed DNA damage checkpoint deficient tissue. For example, the effect of the chemotherapeutic agent can be studied in later screens using (1) non-genotoxically stressed DNA damage checkpoint deficient tissue with the same DNA damage checkpoint deficiency; and/or (2) non-genotoxically stressed tissue with no checkpoint deficiency and/or (3) genotoxically stressed tissue possessing the DNA damage checkpoint function that was missing in the earlier screen, but lacking a different DNA damage checkpoint function i.e. with a different checkpoint deficiency and/or (4) non-genotoxically stressed tissue possessing the DNA damage checkpoint function that was missing in the earlier screen, but lacking a different DNA damage checkpoint function i.e. with a different checkpoint deficiency. The tissue in these further screens can be the same (i.e. same type of tissue from same organism) or different (i.e. different type of tissue and/or from different organism) as was used in the earlier screen. The concentration of the candidate agent(s) can be the same as in the earlier screen or different.

In one embodiment, further screens can be performed using cultured cells that are DNA damage checkpoint proficient or DNA damage checkpoint deficient. The cultured cells are preferably cultured vertebrate cells, most preferably cultured mammalian cells. The further screens using cultured cells can be performed in the absence of genotoxic stress or in the presence of genotoxic stress. The cultured cells can be derived from the same tissue(s) as used in the earlier screen or from different tissue(s). For example, cultured mammalian cells derived from a tumor source can be used in further screens. The effect of the chemotherapeutic agent(s) on the growth or survival of cultured cells can be determined using any method known in the art, including, but not limited to, cell counting and determination of protein content.

In some embodiments, at least some of the steps of the initial screen and/or of any further screen(s) can be performed using automated equipment. For example, the DNA damage checkpoint deficient tissue(s) and the DNA damage checkpoint proficient tissue(s) can be brought into contact with the candidate agent(s) using an automated material handler, such as an automate pipetting machine. For example, in the case of *Drosophila melanogaster* larvae, larvae can be pipetted to individual vials or to individual wells on a microtiter plate using an automated pipetting machine. The automated machine can further pipette candidate agent(s) into the vials or wells. The automated machine can further move the vials or plates using a robotic arm to work stations on a work surface where the vials or plates can be incubated at a predetermined temperature. Analysis of the tissue(s) can also be automated using, for example, automated fluorescence microscope systems in conjunction with fluorescent vital stains. In the case of embodiments of the disclosed methods that use survival or growth of *Drosophila* larvae as an indicator of candidate agent(s) efficacy (see, for example, Example 1), automated imaging systems can be trained to recognize and count larvae, pupae, and empty pupae cases in vials or microtiter plate wells.

The candidate agents of the present invention can be obtained using any of the numerous approaches in combinatorial library methods known in the art, including: biological libraries; natural products libraries; spatially addressable parallel solid phase or solution phase libraries; synthetic library methods requiring deconvolution; the "one-bead one-compound" library method; and synthetic library methods using affinity chromatography selection. See Lam (1997) Anticancer Drug Des. 12:145.

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds can be presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-

1869) or on phage (Scott and Smith (1990) Science 249:386-390; Devlin (1990) Science 249:404-406; Cwirla et al. (1990) Proc. Natl. Acad. Sci. 87:6378-6382; and Felici (1991) J. Mol: Biol. 222:301-310).

Candidate agents suitable for use in the disclosed methods—including synthetic candidate agents and natural candidate agents—include, but are not limited to, those listed by the Developmental Therapeutics Program (DTP) of the National Institutes of Health/National Cancer Institute, the contents of which are incorporated herein by reference in their entirety.

In another aspect, the disclosure provides kits for screening candidate agents according to the methods disclosed herein. The kits comprise one or more containers containing at least some of the physical components used in the methods disclosed herein, and can further comprise printed instructions for the performance of the methods disclosed herein. For example, a kit can comprise at least one of the following: (1) one or more containers containing DNA damage checkpoint deficient and/or DNA damage checkpoint proficient tissue; (2) one or more containers containing agents for exerting genotoxic stress on a tissue (such as a chemical mutagen); (3) one or more containers containing candidate agent(s); and (4) one or more containers containing reagents used to determine the effect of candidate agent(s) on the growth or survival of a tissue (for example, fixatives, vital stains).

Chemotherapeutic agents that selectively reduce the growth or survival of genotoxically-stressed DNA damage checkpoint deficient tissue (including, but not limited to those identified by the methods disclosed herein) can be incorporated into pharmaceutical compositions suitable for administration to an individual with cancer, tumor(s), neoplasms, other conditions involving abnormal cell proliferation, or cell-cycle diseases and disorders. In such compositions, the chemotherapeutic agent is referred to as the "active compound." As used herein the language "pharmaceutically acceptable carrier" is intended to include any and all solvents, excipients, diluents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, dispenser, or kit together with instructions for administration.

In another aspect, the instant disclosure discloses methods of treatment or management of cancer, tumor formation, other conditions involving abnormal proliferation, or cell-cycle diseases or disorders using a therapeutically-effective amount of a chemotherapeutic agent that selectively reduces the growth or survival of genotoxically stressed DNA damage checkpoint deficient tissue (including, but not limited to, chemotherapeutic agents identified by the disclosed methods for identifying chemotherapeutic agents). For example, in one embodiment DNA damage checkpoint deficient tissue, such as cancerous tissue, is genotoxically stressed and treated with a therapeutically-effective amount of a chemotherapeutic agent that reduces the survival or growth of at least part of the genotoxically-stressed DNA damage checkpoint deficient tissue relative to genotoxically stressed DNA damage checkpoint proficient tissue. The chemotherapeutic agent is preferably identified by the disclosed methods for identifying chemotherapeutic agents. The genotoxic stress can be exerted using, for example, a low dose of ionizing radiation such as X-rays. The ionizing radiation can be targeted to the cancerous tissue(s) using, for example, a focused source of X-rays. The genotoxic stress can be exerted prior to administration of the chemotherapeutic agent and/or during administration of the chemotherapeutic agent and/or after administration of the chemotherapeutic agent. Exemplary cancers that can be treated according to the methods provided herein include, but are not limited to, squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningoma, medulloblastoma, schwannoma or epidymoma. Proliferative disorders that may be treated according to the disclosed methods include the myeloproliferative disorders.

EXAMPLES

The following examples are provided for illustrative purposes only and are not intended to limit the scope of the invention.

Example 1

Identification of Chemotherapeutic Agents Using *Drosophila melanogaster* grp Mutants To obtain correctly aged larvae, embryos are collected at Day 0 from wild-type and grp mutant heterozygous adults for approximately 4 hours in the late afternoon or early evening 4 days prior to experiment. The embryos are allowed to hatch into larvae and the larvae are allowed to develop. The grp mutant heterozygote adults carry a grp mutation on one chromosome and a wild-type grp gene on a balancer chromosome. The balancer chromosome also carries a Green Fluorescent Protein (GFP) transgene. Thus, grp mutant homozygous progeny of the heterozygous parents do not express GFP and do not fluoresce when illuminated with 400 nm light, whereas wild-type and heterozygous progeny do carry the GFP transgene and so do fluoresce under 400 nm light.

In the morning of Day 4, food is washed from larvae by using stacked sieves (VWR; USA Standard Testing Sieve: 850, 600, 425, 180 micrometer). The food/larvae are applied to the 850 micrometer sieve and tap water is used to wash food through the sieves; correctly-staged (third instar) larvae go through the 850 micron sieve and are caught in the 600 micron sieve, while younger (smaller) larvae are washed through the 600 micron sieve. For wild-type larvae, larvae are moved into a 35×10 mm petri dish with thin layer of $ddH_2O$. One half of the larval progeny of the grp heterozygous adults and one half of the wild-type larvae are irradiated with 4,000 Rads of X-rays. Larvae (from wild-type parents or from grp heterozygous parents; irradiated or non-irradiated) are then transferred to glass vials containing the candidate agent(s) mixed into a food source. Larvae (from wild-type parents or from grp heterozygous parents; irradiated or non-irradiated) are also transferred to control vials that do not contain the candidate agent(s). Approximately 60 larvae are transferred to each vial. The food source in each vial is cornmeal (7.7% w/v)

and agar (1.2% w/v). This food source serves to nutritionally stress larvae. The vials are then plugged and placed in a 25° C. humidified incubator.

At Day 9, the total number of pupae formed are counted (this gives the percentage of larvae that survived into pupae). In the vials with progeny from grp heterozygous parents, the grp heterozygous pupae and the wild-type pupae are identified by virtue of their expression of GFP and are not counted. At Day 14, the number of empty pupae are counted (indicating the number of pupae that eclosed into adults).

Survival is expressed as the percentage of larvae that form pupae, and the percentage of pupae that eclose into adults. This FIGURE is determined for irradiated wild-type plus the candidate agent(s), irradiated wild-type minus the candidate agent(s), non-irradiated wild-type plus the candidate agent(s), non-irradiated wild-type minus the candidate agent(s), irradiated grp mutants plus the candidate agent(s), irradiated grp mutants minus the candidate agent(s), non-irradiated grp mutants plus the candidate agent(s), and for non-irradiated grp mutants minus the candidate agent(s). Chemotherapeutic agents are identified as candidate agent(s) that selectively reduce the survival of irradiated grp mutant larvae (i.e. reduce the number of larvae that form pupae and/or reduce the number of pupae that eclose into adults).

Example 2

Identification of Colchicine as a Chemotherapeutic that Selectively Reduces the Survival of Irradiated grp Mutant Larvae Using the method exemplified in example 1, the candidate agent colchicine was screened for the ability to selectively reduce the survival of irradiated grp mutant larvae. The concentration of colchicine used was 1.3 µM. The cumulative results of three screens are depicted in FIG. 1. In FIG. 1, SEV–R indicates non-irradiated wild-type larvae, SEV+R indicates irradiated wild-type larvae, grp–R indicates non-irradiated grp mutant larvae, and grp+R indicates irradiated grp mutant larvae (where SEV indicates the Sevelen wild-type strain). The results show that colchicine selectively reduces the survival of irradiated grp mutant larvae.

What is claimed is:

1. A method for identifying chemotherapeutic agents comprising:
   (a) genotoxically stressing a DNA damage checkpoint deficient tissue;
   (b) genotoxically stressing a DNA damage checkpoint proficient tissue;
   (c) contacting said genotoxically-stressed tissues with a candidate agent;
   (d) determining whether said candidate agent reduces the survival or growth of at least part of said genotoxically-stressed DNA damage checkpoint deficient tissue relative to said genotoxically stressed DNA damage checkpoint proficient tissue whereby, a chemotherapeutic agent is identified as an agent that reduces survival or growth;
   wherein said DNA damage checkpoint deficient tissue and said DNA damage checkpoint proficient tissue are intact structures in an organism or structures removed from said organism or portions thereof, provided that the tissues are not single cells in culture; and
   wherein said DNA damage checkpoint deficient tissue comprises grp mutant tissue of *Drosophila melanogaster*, and said DNA damage checkpoint proficient tissue comprise grp wild-type *Drosophila melanogaster* tissue.

2. The method of claim 1 wherein said DNA damage checkpoint deficient tissue comprises grp mutant *Drosophila melanogaster* larval tissue and said DNA damage checkpoint proficient tissue comprises grp wild-type *Drosophila melanogaster* larval tissue.

3. A method for identifying chemotherapeutic agents comprising:
   (a) genotoxically stressing grp mutant larvae of *Drosophila melanogaster;*
   (b) genotoxically stressing grp wild-type larvae of *Drosophila melanogaster;*
   (c) contacting said genotoxically-stressed larvae with a candidate agent; and
   (d) determining whether said candidate agent reduces the survival or growth of genotoxically-stressed grp mutant larvae relative to genotoxically-stressed grp wild-type larvae whereby, a chemotherapeutic agent is identified as an agent that reduces survival or growth.

4. The method of claim 3 wherein said grp mutant larvae and said grp wild-type larvae are nutritionally stressed.

5. The method of claim 3 wherein said larvae are genotoxically stressed using ionizing radiation.

6. The method of claim 3 wherein said ionizing radiation is X-ray radiation.

* * * * *